(12) United States Patent
Feiler et al.

(10) Patent No.: US 6,695,841 B2
(45) Date of Patent: Feb. 24, 2004

(54) PERCUTANEOUS SCAPHOID FIXATION METHOD AND GUIDE WIRE ALIGNMENT DEVICE

(76) Inventors: Frederic C. Feiler, 10 Mesa Dr., Colorado Springs, CO (US) 80906; Mitchell B. Rotman, 90 Aberdeen Pl., Clayton, MO (US) 63105

(*) Notice: Subject to any disclaimer, the term of this patent is extended or adjusted under 35 U.S.C. 154(b) by 0 days.

(21) Appl. No.: 09/922,455

(22) Filed: Aug. 5, 2001

(65) Prior Publication Data

US 2002/0049443 A1 Apr. 25, 2002

Related U.S. Application Data

(63) Continuation-in-part of application No. 09/693,580, filed on Oct. 20, 2000, now Pat. No. 6,589,242.

(51) Int. Cl.[7] .............................................. A61B 17/56
(52) U.S. Cl. ........................... 606/54; 606/97; 606/86
(58) Field of Search ........................... 606/54, 103, 57, 606/58, 96, 97, 87, 130, 86

(56) References Cited

U.S. PATENT DOCUMENTS

| 4,427,005 A | * | 1/1984 | Tener ........................... 606/186 |
| 5,980,526 A | * | 11/1999 | Johnson et al. ............... 606/86 |

* cited by examiner

Primary Examiner—Kevin Shaver
Assistant Examiner—Melba Bumgarner
(74) Attorney, Agent, or Firm—Richard W. Hanes; Hanes & Schutz, P.C.

(57) ABSTRACT

A method and associated apparatus for percutaneous internal fixing of a fractured limb bone comprising, placing the limb in a stabilizing clamp that is transparent to x-ray radiation, demonstrating the fractured bone to be fixed, resolving the course through the fractured bone of an intended fixation device, inserting a guide wire along the resolved course and across the fracture faces of the bone through an alignment conduit in the stabilizing clamp, drilling a pilot hole in the bone through the fracture faces by directing a cannular drill over the guide wire, and introducing a cannular fastening screw within the drilled pilot hole and across the bone fracture site to achieve apposition of the fracture fragments of the bone.

5 Claims, 10 Drawing Sheets

PERCUTANEOUS SCAPHOID FIXATION METHOD AND GUIDE WIRE ALIGNMENT DEVICE

This application is a continuation-in-part of U.S. Application Ser. No. 09/693,580, filed Oct. 20, 2000, now U.S. Pat. No. 6,589,242. The present invention relates to surgical methods and devices for fixation of broken bones and in particular to the percutaneous fixation of a fractured scaphoid bone in the human wrist.

BACKGROUND

The boat shaped scaphoid bone in the human wrist is the largest bone of the proximal row of the carpus on the lateral (radial) side, articulating with the radius, lunate, capitate, trapezium, and trapezoid. The scaphoid is surrounded on 80% of its surface by joint fluid containing fibrinolysin, a substance that dissolves blood clots.

The scaphoid is frequently fractured in young adults through the mid-portion, or "waist" of the bone. Because blood clots are necessary for the healing of bone fractures, the substantial presence of fibrinolysin around the scaphoid inhibits healing of a fracture of that bone unless the fracture fragments are in sufficiently good apposition that joint fluid is prevented from entering the fracture site. Failure to properly fix the bone fragments into apposition will result in a non-union because of the presence in the fracture site of joint fluid.

In addition to an undesirable non-union, resulting from poor apposition, a fracture of the scaphoid through its waist often leads to avascular necrosis or death of the distal pole of the bone. This is because the blood supply to the bone is chiefly through the distal pole and an unhealed fracture at the bone waist cuts off the blood supply to the proximal pole, resulting eventually in severe arthritis and deformity of the wrist.

The traditional conservative treatment of a fractured scaphoid includes the application of a cast to the hand and thumb with the hand in radial deviation in an effort to oppose the fracture ends of the bone. Surgical intervention to fix the scaphoid bone typically includes the use of a screw that requires the expertise of a hand surgeon specialist, and a tedious and difficult surgical exposure.

The percutaneous method and the device of the present invention will allow a less experienced hand surgeon or an orthopedist to fix a scaphoid fracture with a cannular screw. Such simplification of the procedure leads to good apposition of the bone fragments and an overall improved result, including the minimization of surgical exposure of the wrist.

SUMMARY OF THE INVENTION

The present invention provides a simple percutaneous method that incorporates a novel appliance to promote the procedure. The essence of the method is to accurately resolve the required course of a fixation device, such as a cannular screw, and to be able to implant the device along the desired course.

The scaphoid bone is disposed in the wrist at a compound angle that is demonstrated only with an anterior-posterior x-ray and a lateral x-ray of the wrist. Even with the assistance of these x-rays, it is difficult to insert a fixation device that will follow the desired course into the scaphoid bone without substantial surgical intervention, accompanied by possible multiple attempts, or without the aid of an alignment jig, such as the one of the present invention. The apparatus of the present invention comprises a clamp or vise-like device having a pair of opposed relatively movable jaws between which the wrist containing the fractured scaphoid is inserted. Upon closing the jaws of the vise over the dorsal and palmar sides of the wrist, it is held in position so that A-P and lateral view x-rays may be taken. From these x-rays, the desired course of a fixation device may be resolved, including visualization of the angle of the scaphoid, as shown on the A-P view, and its vertical angulation, as shown on the lateral view. Once the course is determined, the single one of a plurality of bore holes in the lower jaw of the vise that is most closely aligned with the desired course is chosen for aligning and positioning a guide wire. Using the chosen bore to support and direct the guide wire, the wire is drilled through skin and subcutaneous tissue into the scaphoid bone, along the direction and at the angle imposed by the aligning bore.

Once the guide wire is drilled into the bone, the wrist is removed from the clamping vise. A small longitudinal incision is made in the tissue on either side of the guide wire and that tissue is then spread in order to accommodate the bit of a drill and the cannular screw that will be inserted into the bone.

A cannular drill bit is passed over the guide wire and a hole coaxial with the wire is drilled to terminate near the proximal end of the scaphoid bone. Following removal of the drill, a cannular lag screw of appropriate length is passed over the guide wire and screwed into the bone, bringing the fracture fragments snugly together in good apposition. The spread tissue is allowed to retract, the guide wire is removed and the incision is closed with a few sutures.

The bone apposition achieved by the accurately placed and well fitted cannular screw prevents joint fluid from entering the fracture site and dissolving the blood clots that are necessary for bone union.

DETAILED DESCRIPTION OF THE PREFERRED EMBODIMENT

The bone fracture fixation method and associated clamping and guide wire alignment apparatus of the present invention are primarily directed toward treatment of a fractured scaphoid bone in the human wrist. However, the invention can be used in the treatment of fractures in other human or animal bones that present the same challenge in determining and following the proper course or angle for the implantation of a fixation device, such as a cannular screw.

The vise and clamping apparatus of the present invention provides a device to stabilize the limb having a broken bone while x-rays or MRI pictures are taken. Then, with the use of the x-rays or MRI, the vise provides alignment means for the insertion of a guide wire that will thereafter pilot the course of subsequent procedures, including drilling and the implantation of a fixation device, such as a screw, across the fracture site of the bone.

Figure 1:
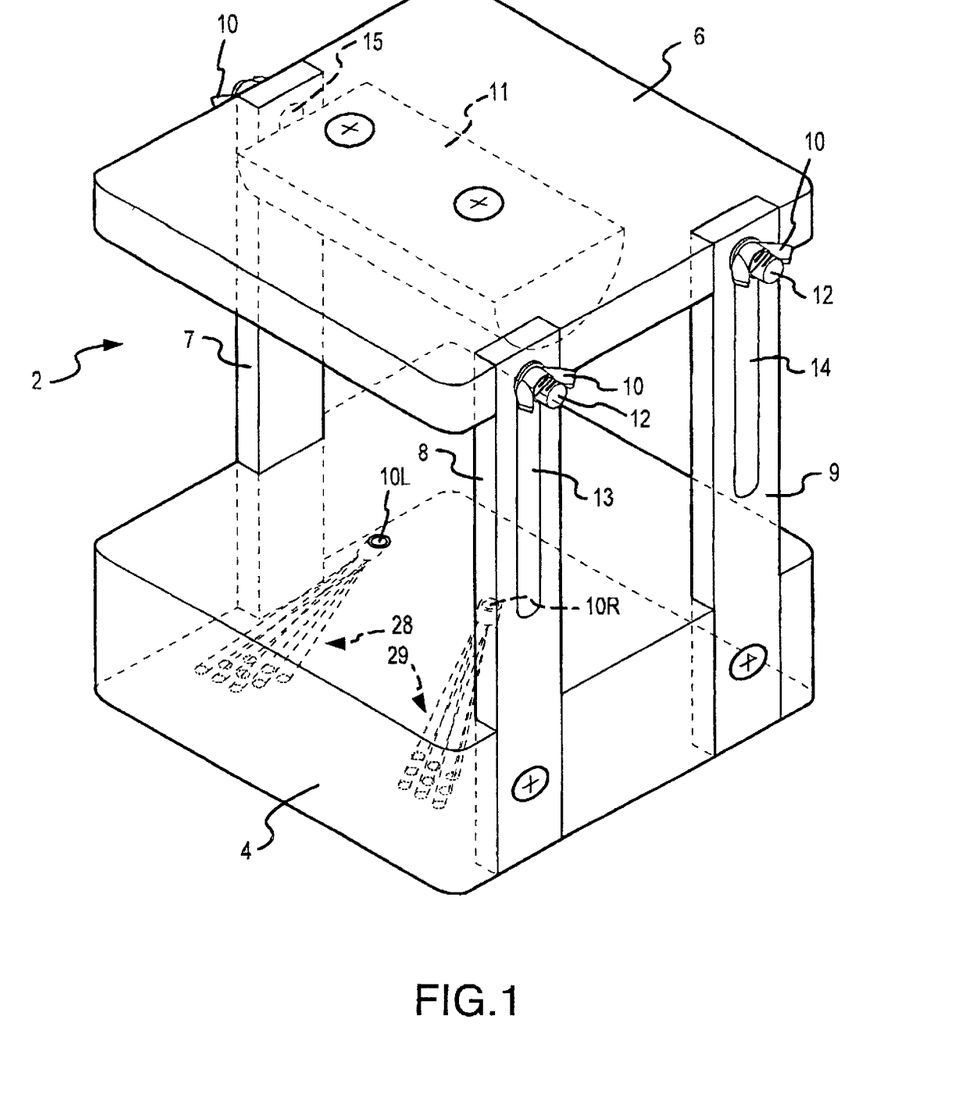
FIG. 1 is a perspective view of the clamping and guide wire alignment apparatus of the present invention.
Figure 2:
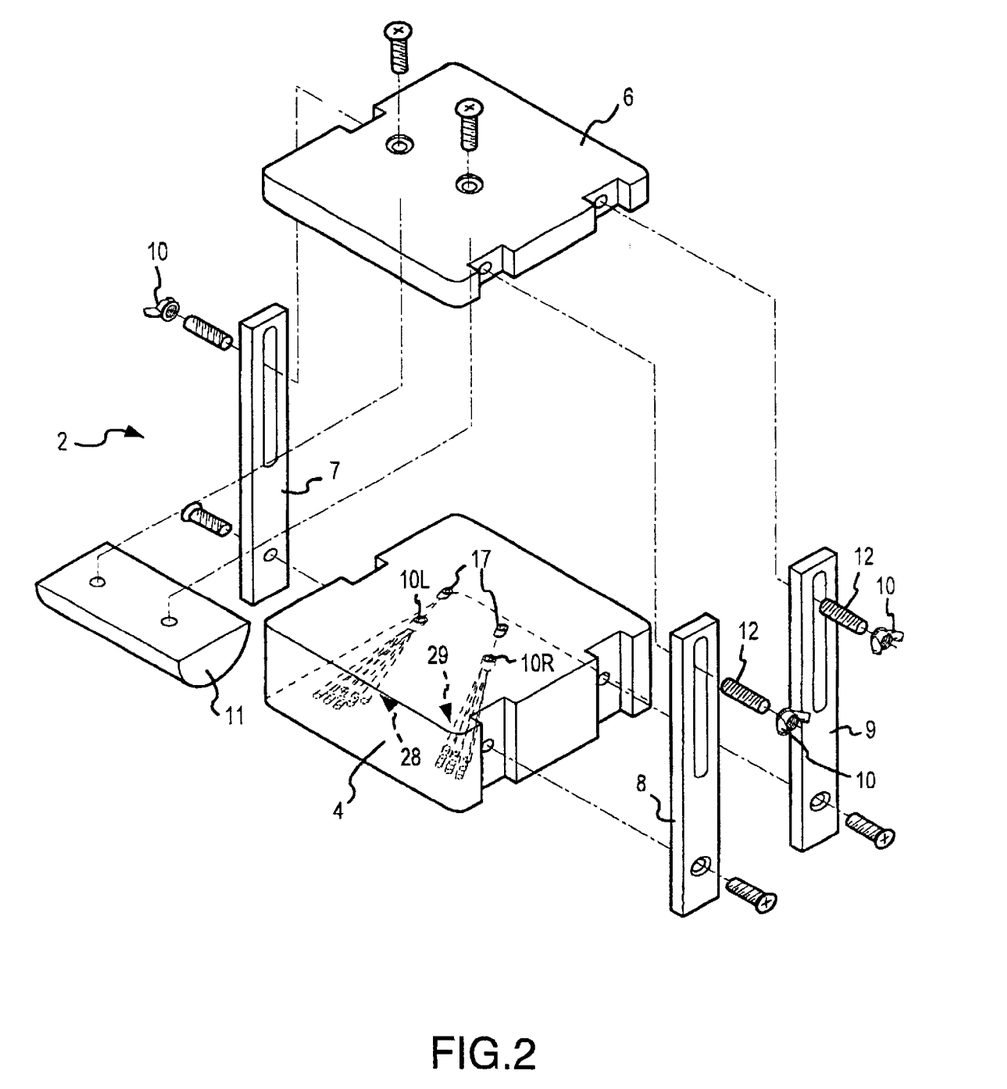
FIG. 2 is an exploded view of apparatus shown in FIG. 1.

FIGS. 1–4 illustrate a preferred form of the limb vise 2. Referring to FIGS. 1 and 2, the vise comprises a pair of substantially parallel spaced apart jaw forming plates 4 and 6. The jaws are moved and positioned with respect to one another by three spacing posts 7, 8 and 9, one end of which are each fixed to the sides of the bottom jaw 4. The other ends of the posts are adjustably secured to the top jaw 6 by wing nuts 10 that thread onto bolt shafts 12 that protrude from the top jaw 6 into grooves 13, 14 and 15 in the spacing posts.

Although threaded rods and nuts are shown in the preferred embodiment of the invention, other forms of adjustable connectors can be used. Such alternative structures might include a traditional vise screw, a ratchet device, or electrical, pneumatic or hydraulically driven adjustable interconnecting linkages. The jaws are said to be substantially parallel because in use they appear to be parallel when casually viewed in their clamping positions on the dorsal and palmar sides of a human wrist 13 (See FIGS. 3 and 4). However, the adjustment mechanism provided by the spacing posts 7, 8 and 9, or its equivalent, permit the plates to be placed in a slightly non-parallel configuration if such a position is necessary to properly secure the particular patient's limb. The jaws 4 and 6 are shown as being substantially similar in their lateral and longitudinal extents, however such resemblance is not necessary. If the particular limb being clamped makes it necessary or desirable for the two jaw plates to have different shapes, those diverse shapes would still be within the scope of the invention. The jaw plates 4 and 6 are constructed from any rigid material that is transparent, or pervious, to x-ray radiation, such as any number of plastics.

The jaw plate 4 that is contacted by the palmar side of the patient's wrist when it is in the clamping position will be referred to herein as the palmar jaw. The opposing jaw 6 will be referred to as the dorsal jaw. The dorsal jaw 6 is fitted on its lower side with a semi-cylindrical pressure pad 11 that makes contact with the dorsal side of the patient's wrist to force the volar (palmar) side of the wrist down against the upper surface 5 of the palmar jaw when the dorsal and palmar jaw plates are brought together. Positioning the volar side of the wrist against, or at least in close proximity, to the surface 5 of the lower clamping jaw is important for taking of proper x-rays of the wrist and for firmly holding the wrist in a properly fixed position for the insertion of a guide wire. Following the taking of x-rays or MRI pictures, the first step in the fixation of the scaphoid bone is to drill a guide wire into the bone across the fracture site. This guide wire acts as the pilot for future drilling and fixing operations. To effectively use the guide wire in subsequent operations, it must be inserted at a point on the wrist and at a compound angle that substantially corresponds to that of the axis of the scaphoid bone. The axis of the scaphoid bone represents a compound angle comprising a horizontal component, as visualized in the A-P x-ray view (FIG. 7), and a vertical component, as visualized in the lateral x-ray view (FIG. 8). The horizontal component angle is generally in the range of 25° to 35° from a vertical sagittal plane through the arm, while the vertical component angle is generally in the range of 40° to 50° from the palmar plane.

Serving as a selection of alignment jigs, a plurality of bores or conduits 28 are disposed in the palmar jaw 4 at a variety of compound angles, one of which will substantially correspond to the compound angle of the axis of the scaphoid bone of the patient. Each of the bores extends from the inferior lower surface 3 of the palmar jaw 4 to the superior surface 5 of the palmar jaw. The bores 28 diverge from a common opening 10L on the superior, or upper, surface 5 of the palmar plate 4 to spaced apart openings, each of which intersect the inferior surface 3 of the palmar jaw 4. Divergence of the bores from the common opening 10L provides a number of jigs in the form of bores, or conduits, each with a distinct compound angle. Surrounding the inside circumference of the opening 10L is a metal collar 17 which serves as a marker on the x-ray views to establish the position of the common opening for the plurality of jigs. It is necessary that this position be ascertained to insure that the wrist is properly positioned to receive the guide wire, as will be later explained.

It has been found that nine guide wire jig bores 28 provide a satisfactory number from which to chose a single one that substantially matches the compound angle of the axis of the scaphoid bone in the patient, however this number of bores is not critical, as there can be more or less. As shown in FIGS. 1 to 5 and 5A, 5B and 5C, the nine bores comprise three sets of three bores each. The front set, seen in the top view, FIG. 5A and the cross sectional view of FIG. 5C, comprises three bores 28a, 28b and 28c having horizontal angular components H, measured from a sagittal plane 30 passing through the common opening 10L, of, for example, 25°, 30° and 35°. The middle set, 28a', 28b' and 28c' and the rear set, 28a" and 28b" and 28c" have the same horizontal component angles.

Figure 5:
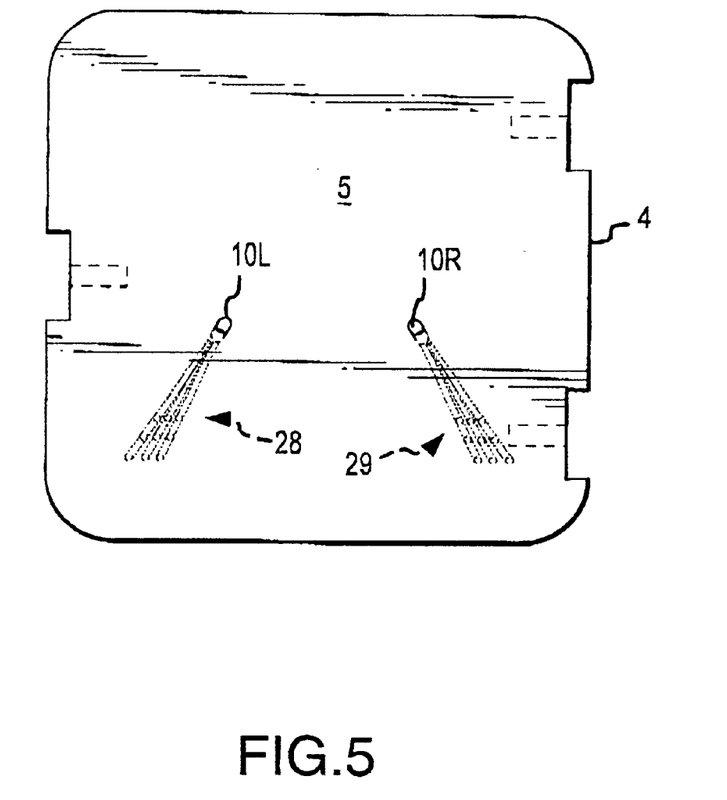
FIG. 5 is a top view of the lower jaw plate of the clamping apparatus.
Figure 5A:
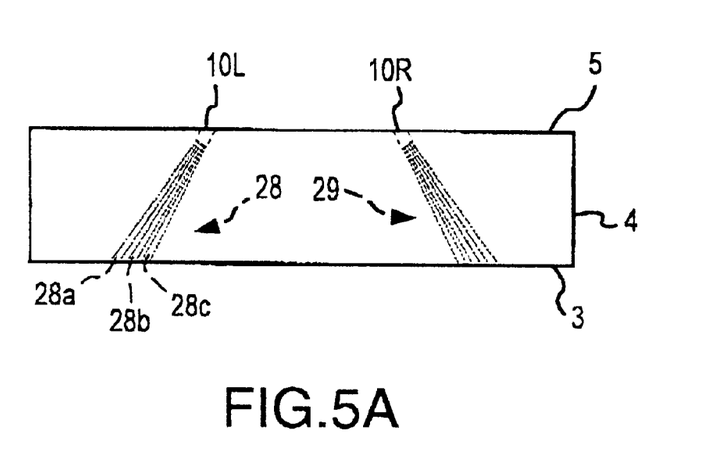
FIG. 5A is a front view of the lower jaw plate of the clamping apparatus.
Figure 5B:
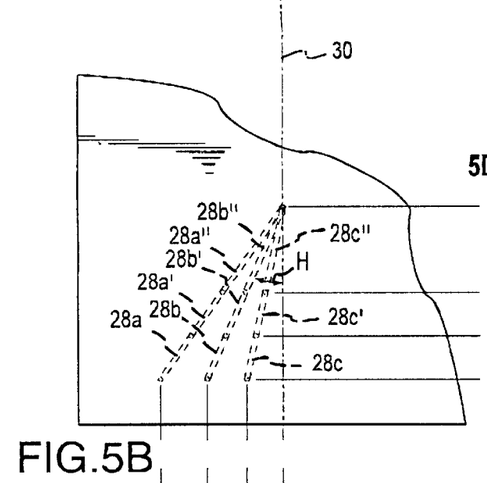
FIG. 5B is a diagrammatic top view of the lower jaw plate with the angles and sizes of the jig bores exaggerated to more clearly illustrate the construction.
Figure 5C:
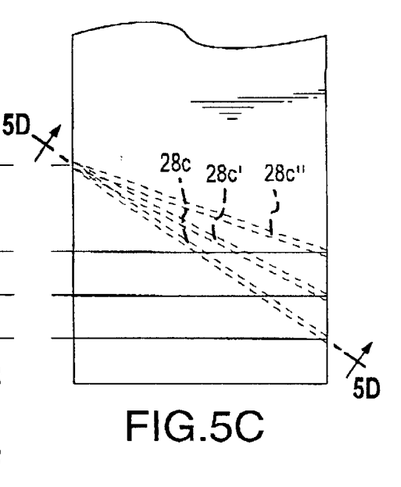
FIG. 5C is an exaggerated diagrammatic side view of the lower jaw plate of the clamping apparatus.
Figure 5D:
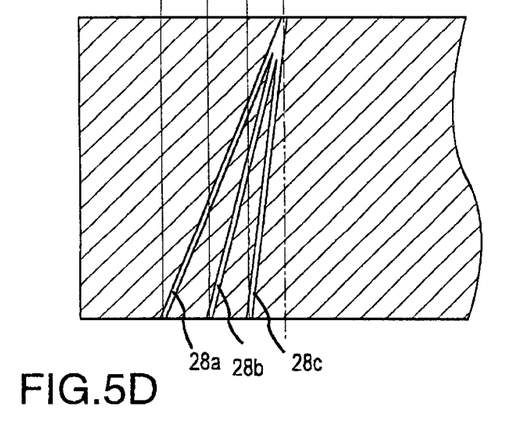
FIG. 5D is a cross sectional view taken along lines 5D—5D of FIG. 5C
Figure 6:
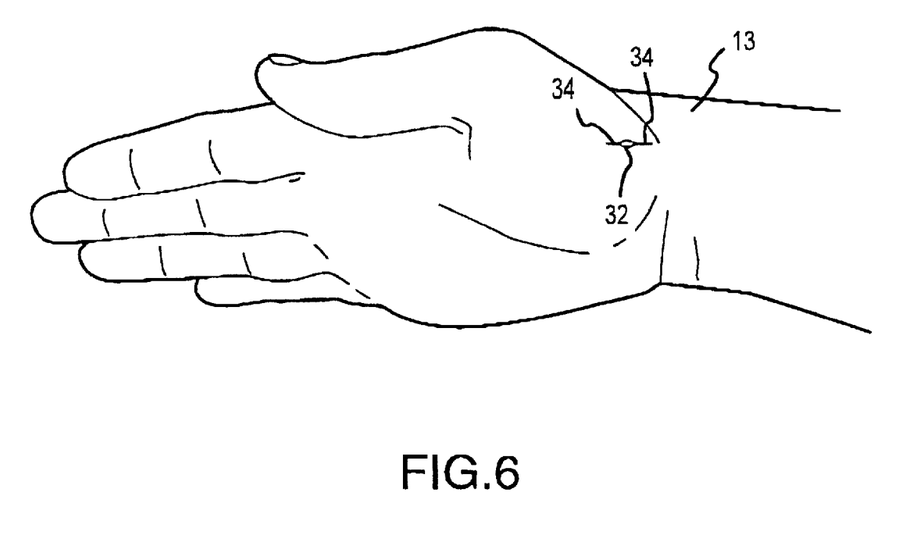
FIG. 6 is a perspective view of a human hand and wrist showing the approximate location on the palmar side of the hand where the guide wire enters the tissue and the location of the incision that is made to permit the drilling and placement of a fixation device.

The bores of the first set 28a, 28b and 28c are all inclined at an angle to the palmar plane of, for example, 25°, as shown diagrammatically in FIG. 5B. The three bores of the middle set, 28a', 28b' and 28c' are all inclined at a vertical component angle to the palmar plane of, for example 45° while the rear set, 28a", 28b" and 28c" are inclined at an exemplary component angle of 50°. These angles and the number of bores are exemplary only, it being apparent that other selections of compound angles, numbers of or grouping of bores are within the teaching of this invention. The respective angles of the bores 28 may be whatever is required to substantially align the guide wire with the pertinent axis of the scaphoid bone, considering the bone's inclination with respect to a palmar plane, as seen in a lateral X-ray view of the wrist, and the horizontal angle of the bone with respect to the sagittal plane, as seen in the A-P view of the wrist.

It is apparent that a single group of bores, such as the three sets of three described above will function for only one wrist, that is, the left or the right. The bores 28 for the left wrist have been discussed above. Accordingly, a second group of bores 29 may be placed in the palmar jaw 4 for use with the other wrist. The bores 29 are configured similarly to the left wrist bores 28, except they are at reverse horizontal component angles, diverging from a common opening 10R in the upper surface of the lower jaw 4 to a plurality of spaced apart openings in the bottom surface of the lower jaw.

The novel percutaneous fixation method of the present invention makes use of the clamping device 2 of the present invention. The purpose of the fixation method and the accessory device 2 is to ultimately implant a fixation device, such as a lag screw 44, accurately across the faces of the fracture fragments so as to achieve maximum apposition of the bone fragments. Snug fitting bone fragments tend to resist the entry of joint fluid into the fracture site, thus eliminating the destruction of the blood clots that are necessary to the union of the bone.

Because the scaphoid bone is relatively small and is disposed in the wrist at a compound angle, it is normally very difficult to visualize the position of the bone with sufficient accuracy that a fixation device may be properly implanted across the fracture site. According to the present invention, and assuming a fracture through the scaphoid bone, a guide wire is drilled into the bone along the same course as that desired for the intended fixation device, such as, for example, a cannular screw or a bone graft. Once the guide wire is properly in place, the remaining steps of the fixation procedure may proceed, using the guide wire as the pathfinder for subsequent steps of the procedure.

Figure 3:
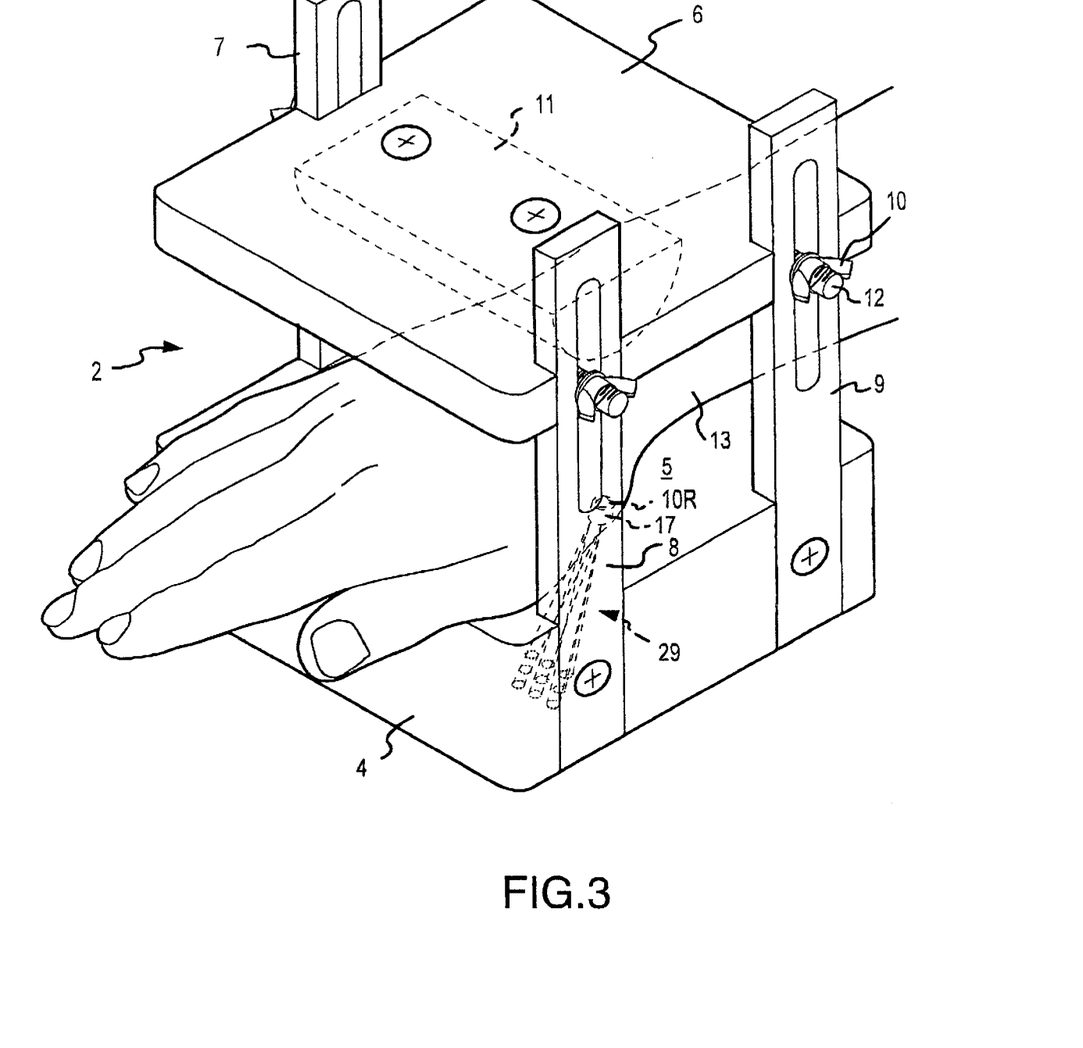
FIG. 3 is a perspective view of the apparatus as it would be viewed with a human wrist clamped into the device.
Figure 4:
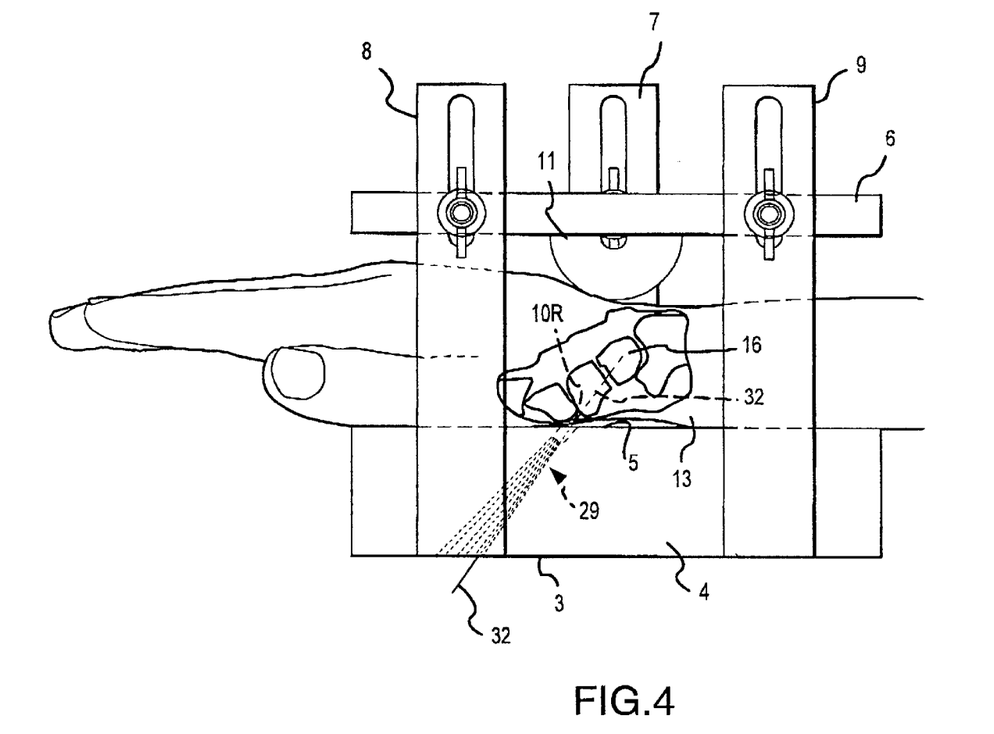
FIG. 4 is a side view of the clamping apparatus of FIG. 3 with portions of the wrist cut away to reveal the scaphoid and associated bone structure of the wrist similarly to what would be shown with a lateral view X-ray.

With the patient's wrist 13 secured in the clamping device 2, as shown in FIGS. 3 and 4, anterior-posterior (AP) and lateral X-ray are taken to demonstrate the position of the scaphoid bone in two planes. On the AP X-ray, a line may be drawn, or a line may just be visualized, along the desired course of the fixation device from the scaphoid distal pole through the bone fracture site at the point where the fixation device should pass.

The lateral view X-ray is used to determine the vertical angle from the horizontal of the scaphoid bone, as shown in FIG. 4. When the vertical angle is known, the course of the guide wire in the vertical plane is established. Next, using the measured angle of bone inclination and the AP alignment of the scaphoid bone a particular one of the applicable group of bores is selected for piloting the guide wire into the scaphoid bone 16.

Figure 10:
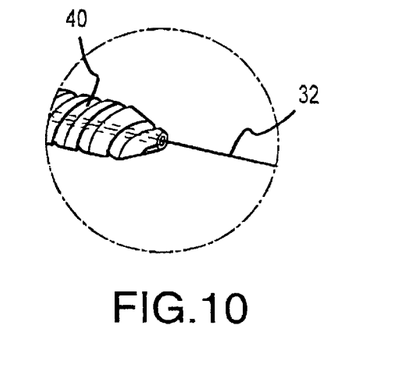
FIG. 10 is an enlarged detail of the tip end of the drill taken within the circle in FIG. 9.
Figure 11:
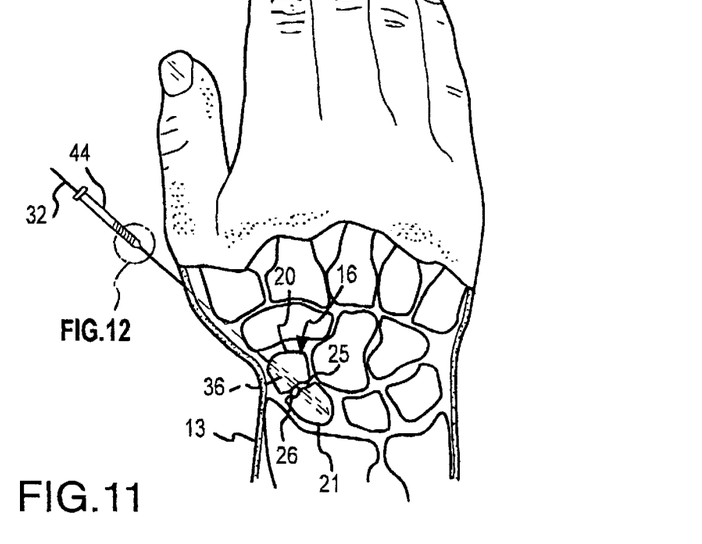
FIG. 11 is a view similar to that of FIG. 9, showing the insertion of a cannular lag screw into the drilled hole in the scaphoid that was created by the drill bit of FIG. 10.

When the bore selection is made, a guide wire 32 is inserted into the chosen bore hole. The wire is then drilled into the wrist tissue, the volar distal pole 20 of the scaphoid bone and across the fracture faces 25 and 26 to the dorsal proximal pole 21 of the scaphoid, as shown in FIGS. 10 and 11. Once the guide wire 32 is implanted into the scaphoid 16, the guide wire is severed between the wrist and the superior surface 5 of the palmar jaw, allowing the vise 2 to be loosened and the wrist removed therefrom for completion of the fixation procedure.

Figure 7:
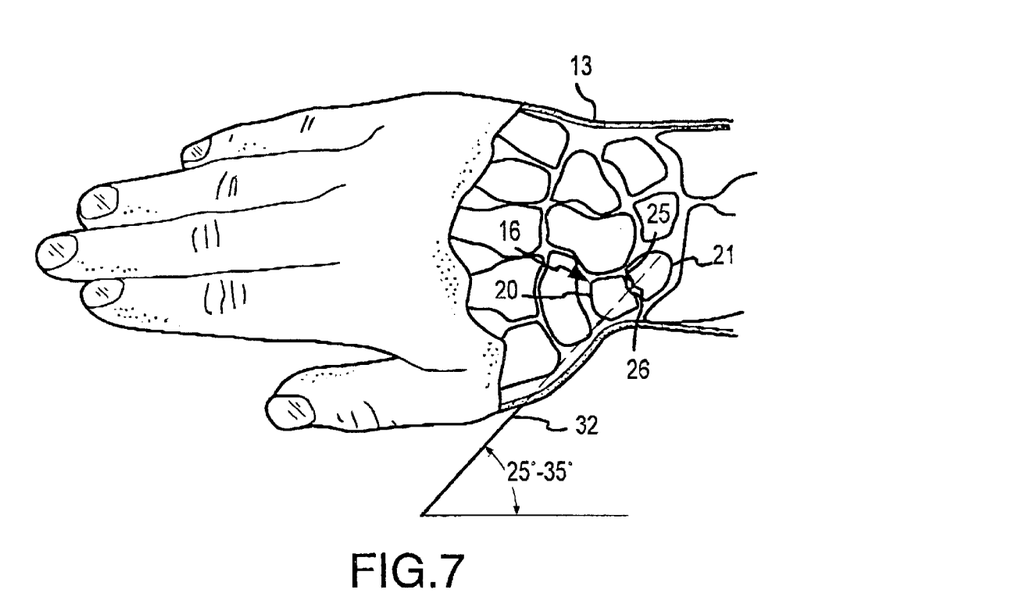
FIG. 7 is a posterior (dorsal) view of the human hand and wrist with skin muscles and tendons broken away to reveal the bone structure as it would appear in an anterior-posterior (AP) x-ray, illustrating a fractured scaphoid and the necessary horizontal angular alignment of a pre-fixation guide wire.
Figure 8:
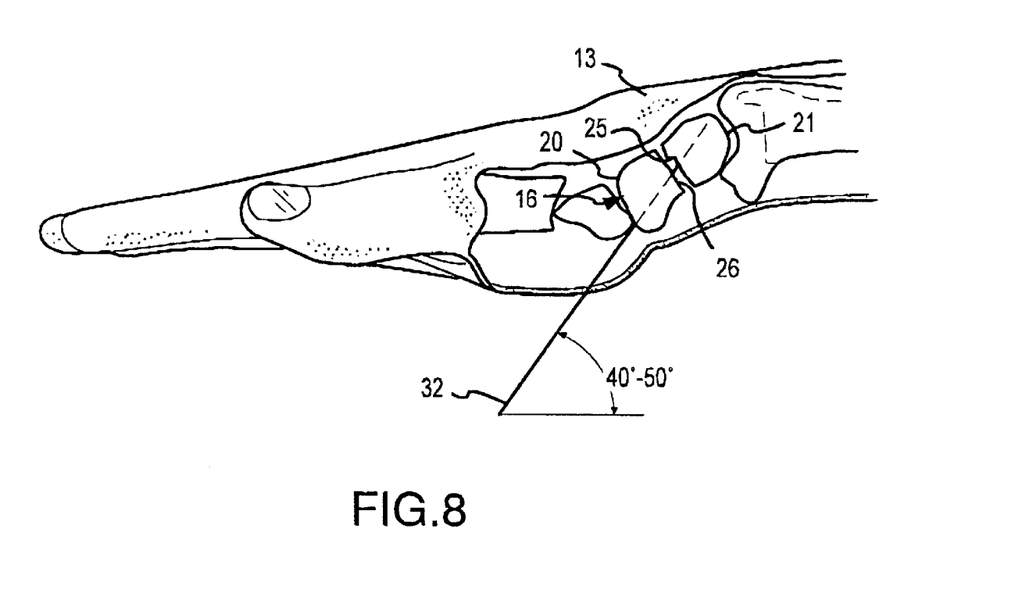
FIG. 8 is a lateral view of the human hand and wrist with skin muscles and tendons broken away to reveal the bone structure as it would appear in a lateral x-ray, illustrating the fractured scaphoid and the necessary vertical angular alignment of a pre-fixation guide wire.
Figure 9:
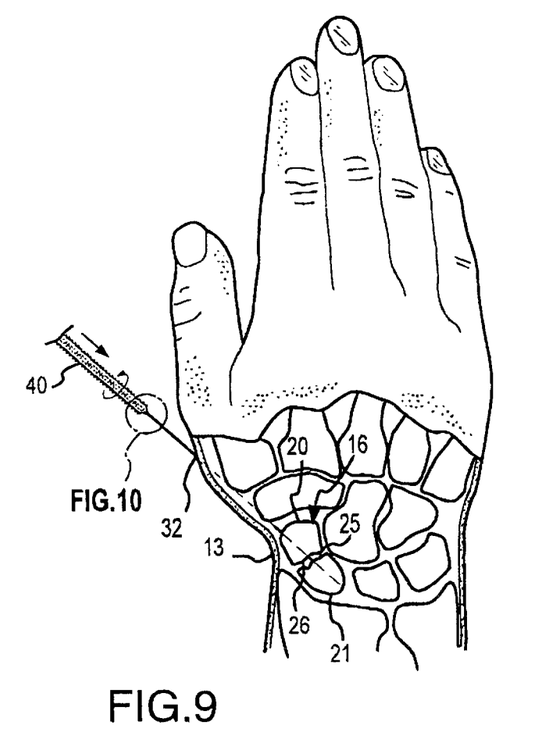
FIG. 9 is a view similar to that of FIG. 7, and illustrating a portion of a cannular drill bit being inserted over the guide wire that has previously been inserted into the scaphoid bone.
Figure 12:
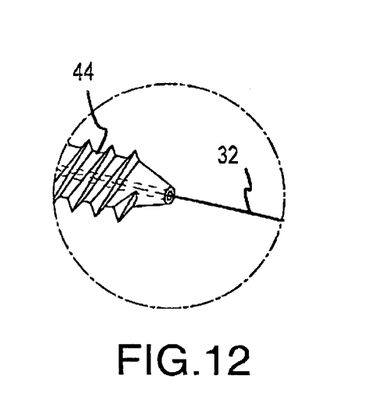
FIG. 12 is an enlarged view of the tip end of the cannular lag screw as it is passed over the guide wire.
Figure 13:
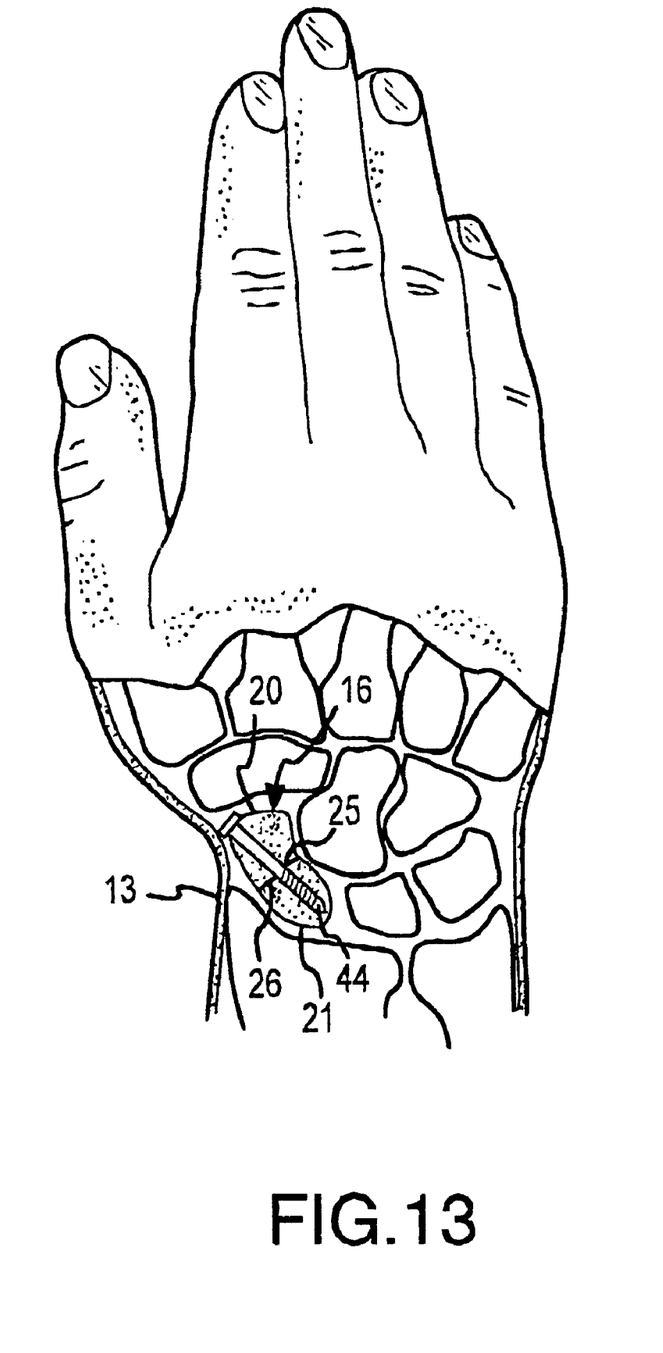
FIG. 13 is a view similar to that of FIG. 11, but illustrating the end result of the process, where the scaphoid bone fragments have been secured in apposition by a lag screw type of final fixation device.

A small longitudinal incision 34 is made proximally and distally on either side of the guide wire 32, as illustrated in FIG. 7. Next, as shown in FIGS. 10 and 11 a cannular drill bit 40 is passed over the guide wire 32 and through the incision 34 prepared in the tissue. Following the guide wire 32, the drill bit 40 creates a pilot hole 36 in the scaphoid along the desired course of the fixation device of sufficient diameter and length to accommodate such a device 44. The drill bit 40 is withdrawn and the cannular screw 44 is passed over the guide wire 32 and screwed into the scaphoid bone 16, as shown in FIGS. 12, 13 and 14. When the screw has been fully seated and the bone fragments are pulled together in apposition (FIG. 14), the guide wire 32 is removed and the small incision 34 is closed with a few sutures.

Employment of the apparatus 2 and the method of the present invention result in good apposition of the bone fragments with reasonable assurance that a union of the fragments will take place, since joint fluid has thus been isolated from the fracture site.

We claim:

1. A surgical appliance for repairing fractures of the scaphoid bone in a human wrist comprising, vise means, having upper and lower spaced apart jaws that are transparent to x-ray radiation and are relatively movable toward and away from one another for retaining there between at least a portion of a human wrist, the lower jaw having spaced apart inferior and superior surfaces, means interconnecting the upper and lower jaws for fixing the spacing between the jaws, a plurality of bores through the lower jaw that diverge from a common intersection with the superior surface to spaced apart intersections with the inferior surface of the lower jaw.

2. The appliance of claim 1 and further including a second plurality of bores through the lower jaw that diverge from a second common intersection with the superior surface to spaced apart intersections with the inferior surface of the lower jaw.

3. A surgical tool for aligning fixation apparatus incident to the repair or fusion of human limb bones, comprising, a vise, having relatively movable x-ray pervious first and second spaced apart jaws for retaining a portion of a limb there between and where the second jaw has upper and lower spaced apart surfaces, means interconnecting the jaws and operable to fix the spacing there between at least one conduit extending through the second jaw and directed toward the limb for receiving a guide wire and where the at least one conduit is a plurality of conduits that diverge from a common intersection with the upper surface to spaced apart intersections with the lower surface of the second jaw.

4. The tool of claim 3 and further including an x-ray impervious ring around the common intersection with the upper surface of the second jaw.

5. An appliance for aligning a wire guide preparatory to insertion of a fixation device for repairing limb bone fractures, comprising, first and second substantially parallel planar jaws for clamping there between a limb containing a fractured bone, each of said jaws having upper and lower substantially mutually parallel surfaces, adjustable connecting means for interconnecting and selectively fixing the spacing of the jaws, one from the other, at least one straight wire guide passageway in communication with the upper and lower surfaces of the second jaw, the passageway forming an acute angle with the upper and lower surfaces.

* * * * *